United States Patent [19]

Rabaud et al.

[11] Patent Number: 5,223,420
[45] Date of Patent: Jun. 29, 1993

[54] ELASTIN-BASED PRODUCT, A PROCEDURE FOR ITS PREPARATION AND ITS BIOLOGICAL APPLICATIONS; IN PARTICULAR AS BIOMATERIALS AND ARTIFICIAL SUPPORTS

[75] Inventors: Michel Rabaud, Talence; Francoise Lefebure Clement, St Medard en Jalles; Henri Bricaud, Cambes; Roland Schmidthaeusler, Illkirch-Graffenstaden, all of France

[73] Assignee: Institut National de la Sante et de la Recherche Medicale, Paris, France

[21] Appl. No.: 507,102

[22] PCT Filed: Mar. 3, 1986

[86] PCT No.: PCT/FR86/00068
 § 371 Date: Oct. 29, 1986
 § 102(e) Date: Oct. 29, 1986

[87] PCT Pub. No.: WO86/05097
 PCT Pub. Date: Sep. 12, 1986

Related U.S. Application Data

[63] Continuation of Ser. No. 930,268, Oct. 29, 1986, abandoned.

[30] Foreign Application Priority Data

Mar. 1, 1985 [FR] France .............................. 85 03057

[51] Int. Cl.⁵ ...................... A61K 9/70; A61K 37/12; C12N 5/00

[52] U.S. Cl. ..................................... 424/425; 424/484; 435/240.23; 435/240.2; 514/21; 530/353; 530/382; 530/383

[58] Field of Search ................... 514/21; 424/425, 484; 530/353, 382, 383; 435/240.23, 240.2

[56] References Cited

U.S. PATENT DOCUMENTS 4,614,794 9/1986 Easton et al. ...................... 530/356

OTHER PUBLICATIONS

Burleson, R. L., et al. (1978) J. Surg. Res. 25, 523–529.
Pool, J. G. et al. (1965) New Eng. J. Med. 273, 1443–1447.
Thornton, J. W., et al., (1984) Burn Wound Coverings 1, 147–159.
Burke, J. F. (1984) Surg. Sci. Ser. 2, 311–315.
"The Condensed Chemical Dictionary", (G. G. Hawley, ed), Van Nostrand Reinhold, New York, 1977, pp. 16 and 464.
Burleson, R., et al. (1972) Surgery 72(2), 315–322.
Burleson, R. L., et al. (1979) Chem. Abst. 90:84529y.
Thornton, J. W., et al. (1984) Chem. Abst. 101:149225p.
El-Far, M. A., et al. (1985) Chem. Abst. 103:2997z.
Rabaud, M., et al. (1986) Chem. Abst. 105:58551h.

Primary Examiner—Charles L. Patterson, Jr.
Attorney, Agent, or Firm—Fleit, Jacobson, Cohn, Price, Holman & Stern

[57] ABSTRACT

The subject of the invention is an elastin-based product consisting of an adduct containing elastin and at least one protein which can be coagulated and/or activated by thrombin.

32 Claims, 6 Drawing Sheets

ELASTIN-BASED PRODUCT, A PROCEDURE FOR ITS PREPARATION AND ITS BIOLOGICAL APPLICATIONS; IN PARTICULAR AS BIOMATERIALS AND ARTIFICIAL SUPPORTS

This application is a continuation of application Ser. No. 06/930,268, filed Oct. 29, 1986, abandoned.

The subject of the invention is an elastin-based product, endowed, especially, with properties of elasticity and robustness.

The invention also relates to a procedure for its preparation as well as to the biological applications of this product, in particular, for the preparation of biomaterials and supporting materials which may be used, in particular, as artificial tissues or supports for cell cultures.

It is known that elastin is a constituent of the elastic components of an organism, in particular, of the lungs, skin, arterial walls and umbilical cord.

It is a protein of the scleroprotein type, generally resistant to the action of acids, alkalis and proteolytic enzymes, with the exception of elastase, for which it is a specific substrate and is degraded by it.

In vivo, elastin is protected from the action of elastase, especially by complexes between elastase and inhibitors in the serum. However, in various pathological processes of inflammatory origin or related to age, such as pulmonary emphysema or atherosclerosis, degradation of elastin, probably due to elastase, is observed from an early stage of the disease onwards.

In the course of earlier work, some of the co-inventors of the present invention demonstrated the existence in vitro of the complexes between elastase and inhibitors in the serum formed in vivo in the plasma or the serum, and have studied their capacity to bind to elastin and their elastolytic activity induced by raising the pH from 6 to 8.6.

In the course of the study of a possible elastinolytic activity in human serum or plasma, it had been reported that the adsorption of plasma or serum to elastin, when incubation was carried out at 37° C. in a 0.2M acetate buffer, pH 6, which was 1 mM with respect to the acetates of calcium, magnesium and manganese, is accompanied by a visible modification of the appearance of the protein which loses its granular character and becomes flocculent.

Research designed to lead to an understanding of this phenomenon had led the inventors to the observation that, by working under certain conditions, it is possible to form and isolate a new elastin-based product endowed with remarkable properties of both strength and elasticity. Another particularly advantageous feature is its plasticity.

Thus, the subject of the invention is to furnish a new elastin-based product, the properties of which, in particular its flexibility and robustness, make it possible to prepare a biomaterial or a supporting material in various forms, especially in the form of membranes, connecting pieces or filaments, displaying satisfactory properties for various biological applications.

Another subject of the invention is to provide a procedure for the preparation of this product with the required properties under convenient working conditions.

The invention also relates to the exploitations of the properties of this product for the preparation of biomaterials and supporting materials which cater for needs of great importance, for example, for the repair of tissues or the development of supports for cell cultures.

The product according to the invention derived from elastin is characterised in that it consists of an adduct containing elastin and at least one protein of the type which can be coagulated and/or activated by thrombin.

In the context of the present invention, it is understood that the term elastin covers native or mature elastins, their derivatives and elastins modified, especially, by hydrolysis.

In an advantageous manner, a product of this type possesses a high chemical resistance and the structural properties of high elasticity and great strength. In addition, it displays great plasticity and flexibility as well as properties of impermeability and it can also be moulded, which confers on it great importance, especially for the purposes of biological applications.

In one of its forms the elastin-based product of the invention consists of an adduct containing elastin and soluble fibrin.

It will be recalled that soluble fibrin is formed as an intermediate from fibrinogen in the process of coagulation, according to the following scheme:

A preferred product consists of an adduct formed from fibrinogen and elastin.

Another preferred product consists of an adduct formed from plasma and elastin.

According to another form of the invention, the elastin-based product also contains fibronectin.

It has been demonstrated that fibronectin binds specifically to elastin and thus participates in the formation of the adduct, the plastic properties of which are thus considerably improved. The fibronectin may be isolated from blood, in which case it is prepared preferentially by cryoprecipitation according to the technique by Pool, J. G. and Shannon, A. E. and described in New Eng. J. Med., 465, 273, 1443–1447. it may also be added in a form purified from placental blood or from fractions of cells in culture.

Adducts of the type containing fibronectin can also be advantageously prepared from elastin and cryoglobulins.

Appropriate cryoglobulins contain fibrinogen and fibronectin in variable proportions. For example, the fraction called anti-hemophilic A, lyophilised, which contains about 10 to 15 g/l (i.e. per liter of product reconstituted in buffer) of fibrinogen and about 2 to 4 g/l of fibronectin.

Another fraction is obtained by the procedure for extracting concentrated Factor VIII and contains about 9 to 20 g/l of fibrinogen and about 10 to 14 g/l of fibronectin.

Yet another fraction consists of a lyophilised protein complex containing, in particular, about 50 to 90 g/l of fibrinogen and 8 to 15 g/l of fibronectin.

This complex, called Transglutin (described, in particular, by Thiebaut et al. in La Nouvelle Presse Médicale of 11th Sep. 1982, 11, No. 35 page 538) contains, in addition, 590±250 u/ml of factor XIII, with about 95±35 g/l of total protein and about 35 to 90% of protein coagulable by thrombin.

Soluble fibrin, or the derivatives from which it is produced, and elastin are of animal or human origin. In particular, the elastin is derived from bovine nuchal ligament, human aorta or the umbilical cord.

The adducts of the products of the invention display great stability. Thus, it is possible to store them for several months in the presence of standard biological preservatives such as sodium azide or sodium ethylmercrylthiosalicylate.

Depending on the properties that one wishes to reinforce or confer on the products, various appropriate additives may be incorporated, insofar as these additives do not affect the affinity of soluble fibrin for elastin in the adduct formed and the resultant properties. In the remainder of the text, the products thus prepared will also designated by the special description of biological patch.

Preferred additives include compounds intended to reinforce the mechanical properties, such as collagen, or cellulose derivatives or calcium alginate.

The addition of compounds exhibiting a vulcanising action makes it possible to improve elasticity. Such substances include sulfur compounds, in particular of the sodium ethylmercrylthiosalicylate type mentioned above, or, preferably, thiourea, since advantageously it does not contain mercury. Moreover, sterilisation by γ-rays also induces, in addition to cross-linking similar to the original lattice, a process of vulcanisation independent of the addition of a vulcanising agent without impairing the qualities of the product.

Furthermore, other adhesive proteins such as the FVIII (anti-hemophilic A) complex, the von Willebrand factor, thrombospondin, laminin which are to be found in the blood, the vascular wall, the placenta or fractions of cells in culture may be advantageously added to improve the mechanical, elastic and adhesive properties of the biomaterial.

The procedure of the invention for the preparation of the elastin-based products defined above is characterised in that it includes a step in which fibrinogen or a mixture containing it, in particular plasma, and elastin are incubated in the presence of thrombin and $Ca^{++}$, advantageously under essentially physiological conditions, in particular with respect to temperature and pH, with the result that thrombin, activated by $Ca^{++}$ ions, transforms fibrinogen into soluble fibrin, an event which is reflected in the appearance of a flocculent or fibrillar product in the reaction mixture.

The temperature, the $Ca^{++}$ ion concentration and the pH are seen to be the dominant factors, implying the involvement of an enzyme system.

The incubation step is preferably carried out at about 37° C.

The products used are equilibrated preferably at a pH in the neighbourhood of 7.4.

The content of free $Ca^{++}$ ions corresponds, advantageously, to its content in vivo, namely of the order of 2 mM.

The elastin used is of animal or human origin and is derived from the organs mentioned above.

In the variant including the use of plasma as the source of fibrinogen, the plasma is obtained from blood collected in the presence of an anticoagulant usually contained a citrate buffer and ethylene diamine tetraacetic acid, which complex $Ca^{++}$ ions, or also heparin.

In order to release the $Ca^{++}$ ions for the activation of thrombin so that fibrinogen maya be transformed as desired, the plasma is subjected to a preliminary treatment consisting advantageously of a dialysis.

The dialysis operation is carried out against a buffer with properties similar to those of a physiological medium, in particular the pH and $Ca^{++}$ ion content of which meet the demands set out above. Elastin is also equilibrated with this buffer.

Of the buffers of this type which are particularly suitable, mention will be made of a phosphate buffer, pH 7.4, of the following composition: 1 mM phosphate, 150 mM NaCl, 2 mM $Ca^{++}$, 1 mM $Mg^{++}$.

During dialysis, the reagent complexing $Ca^{++}$ is removed from the dialysis compartment and the fibrinogen is transformed into soluble fibrin, then into insoluble fibrin according to the scheme outlined above.

Dialysis is advantageously carried out for about at least 60 minutes.

The incubation step, carried out under the conditions defined above, leads immediately, that is within several minutes, to the physical transformation of elastin from a granular powder to a fibrillar state, with the appearance of lacerated connective tissue.

By agitation of the reaction mixture, fibres are formed which are separated, for example, by centrifugation.

In order to have available biomaterials which can be used in the applications envisaged below, the following procedure has been adopted:

To the elastin are added successively the additives which improve, in particular, the elastic and mechanical properties as well as the reticulation of the desired product, then fibrin or a substance or mixture from which fibrin may be derived. When fibrinogen or a substance containing it is used as fibrin source, thrombin is added to the reaction mixture in order to transform the fibrinogen into fibrin. The mixture is then incubated at a temperature of about 37° C. until a biological patch is formed. Satisfactory mixing of the various constituents added to the mixture is ensured by the use of a mixer of the VORTEX type.

The elastic and mechanical properties confer on the patch a malleable character which makes it possible to produce membranes surfaces of the form and dimensions desired for a given application.

It is thus possible to obtain biological patches in the form of connecting pieces, filaments and membranes, or materials possessing the form of the matrix used to prepare them.

The biological patch obtained is removed from the mould, dried, if necessary, on filter paper for example to remove the excess water used in the preparation, and used as such.

Patches may be stored in alcohol, ethanol in particular, and sealed in an impermeable envelope under an inert gas such as nitrogen. Advantageously, the storage envelope is irradiated in order to sterilise the patch, a treatment which also improves vulcanisation and reticulation.

When the patch is used as a membrane support for cell culture, it is preferable to store and sterilise it without removing beforehand the excess water used in the preparation which it still contains.

When it is to be used as biomaterial, artificial tissue, a constituent of tissue repair or such like, it is advantageous to store the patch in alcohol. Just prior to use the excess alcohol is removed with filter paper, for example, then the patch is soaked in several baths of physiological serum.

It is also to be noted that the patch of the invention can be formed in situ in the media used for cell cultures.

Study of the properties of the elastin-based product of the invention has, in addition, made it possible to demonstrate their high stability. Owing to their properties of strength and elasticity advantageously combined with those of biocompatability and impermeability, the elastin-based products according to the invention can be used especially as biomaterials.

The invention thus also relates to new biomaterials including adducts or biological patches based on elastin such as those specified above.

Of the preferred biological patches according to the invention, particular mention will be made of the one containing essentially elastin, fibrin, fibronectin and collagen and the one containing, additionally, thiourea.

These biomaterials are of great importance more especially as "artificial skins" or "artificial connective tissues".

They constitute, in particular, elements of support or reinforcement or seals, used in combination with biocompatible adhesives and/or sutures, and particularly valuable in surgery.

Of the biocompatible adhesives, particular mention will be made of Transglutin which also possesses properties of adhesive strength.

It should be pointed out that the thrombogenic properties of these biomaterials are conducive to their being used as agents to repair tissue injury. In fact, the interaction of the constituents of blood, platelets and proteins involved in coagulation, at the interface between the blood and a biological patch causes the platelets to be activated, adhere and secrete the contents of their granules, thus leading to the formation of platelet aggregates which enhance the binding of the adduct at the site of tissue injury.

The products according to the invention play the role of temporary supporting tissues which first initiate and then direct the process of tissue repair. These properties make it possible to apply these products in all types of surgery, in particular digestive, vascular, urinary, genital and obstetrical, maxillofacial and plastic, dermatological, fetal and neonatal, as well as veterinary.

They can be used to compensate for certain losses of tissue and, in particular, to treat burns.

In accordance with another aspect of the invention, the products constitute supporting materials which are of particular interest as supports for cell culture.

Cultures of smooth muscle cells, fibroblasts, epithelial cells and endothelial cells can be grown in high yields.

They can also be used as culture transplants, constituting dermal bases on which are seeded, for example, epithelial cells which multiply, with high efficiency, to form an epidermis. These grafts are transplantable to the organism of the recipient on account of their biocompatibility.

As supports they can also be used for grafting biological substances such as enzymes in particular, and both specific and general inhibitors of the enzymes which are responsive for the proteolysis of elastin, collagen, fibrinogen and fibronectin.

Supports of this type include, for example, enzymes such as $\alpha$-2 macroglobulin, aprotinin, $\alpha$-1-antitrypsin or anti-plasmins incorporated into the elastin-based products.

According to another aspect, the invention also relates to kits containing the elements necessary for carrying out cell culture or tissue repair.

A preferred type of kit consists of a receptacle, a Petri dish, for example, containing the biological patch of variable thickness depending on the cell culture to be carried out.

Another type of kit consists of the patch advantageously provided in its storage envelope and a flask containing the biological adhesive, Transglutin in particular.

Other properties and advantages of the invention are reported in the examples which follow relating to the preparation of products according to the invention and to their applications as "artificial tissues".

BRIEF DESCRIPTION OF THE DRAWINGS

In these examples, reference is made to FIGS. 1 and 5 which present respectively:

photographs illustrating the formation of an adduct between elastin and fibrin (FIGS. 1a to 1d).

curves showing the variation, during dialysis against a phosphate buffer, in the content of $Ca^{++}$ and $Mg^{++}$ ions as a function of time (FIG. 2) and as a function of the $Ca^{++}$ content of the dialysis buffer (FIG. 3).

curves showing the formation of fibrinopeptides A and the diminution of the fibrinogen content as a function of time (FIG. 4), and the time of formation of the adduct as a function of the quantity of thrombin added (FIG. 5).

The source of the materials used is specified below.

Elastin from bovine nuchal ligament supplied by Worthington and obtained from EUROBIO, Paris is used.

Elastin from human aorta is prepared according to the method of LANSING described by LEPPERT et al. in Arch. Biochem. Biophys. 1983, 222, 53–58. The elastin is washed thoroughly, then swollen in an appropriate buffer at 37° C. just before being used.

The samples of human plasma are prepared in the presence of citrate and maintained at −40° C.

Human fibrinogen (grade L) is obtained from KABI DIAGNOSTIC, Stockholm, Sweden. Radio-labelling is carried out according to the method of GREENWOOD et al. described in Biochem. J. 1963, 39, 114–123. Ten milligrams of fibrinogen is dissolved in 1 ml of 0.1M PBS, pH 7.5. The fibrinogen is labelled with 500 $\mu$Ci of iodine 125. To prevent reduction of the labelled fibrinogen by metabisulfite, the reduction step is not carried out and, immediately after oxidation of I− to I+, the crude product is applied directly and rapidly to a gel filtration column (Sephadex G 50). $5 \times 10^6$ cpm/mg of $^{125}$I-fibrinogen are obtained.

As human thrombin, the product supplied by Ortho Diagnostic Systems, Inc., with a titre of 50 u/ml is used.

Hirudin is a product supplied by Sigma and obtained from OSI Paris.

The levels of $Ca^{++}$ and $Mg^{++}$ are determined by atomic absorption.

The fibrinogen concentrations in the plasma are measured according to the method of von CLAUSS et al. described in Acta Hemat. 1957, 17, 237–247, and the citrate content by the enzymatic method of ZENDER et al. (Clin. Chim. Acta 1969, 24, 335-340).

Human fibrinopeptide A is measured by using the immunoenzymological assay on a solid phase described by SORIA et al. in Thromb. Research 1980, 20, 425-435.

EXAMPLE 1

Preparation of an adduct derived from elastin of bovine nuchal ligament and soluble fibrin obtained from the Factor VIII fraction of cryoglobulins.

In a 5 ml hemolysis tube 50 mg of elastin are carefully washed with phosphate buffer, pH 7.4 (1 mM phosphate, 150 mM NaCl, 2 mM $Ca^{++}$ion, 1 mM $Mg^{++}$). The washing buffer is removed by centrifugation.

The elastin is placed in 1.5 ml of phosphate buffer. A preservative is added (for example, sodium azide, at 200 mg/l).

The elastin is dispersed by means of a VORTEX mixer, then 0.5 ml of Factor VIII (containing 15 mg of fibrinogen and 8 mg of fibronectin in 1.5 ml of phosphate buffer which also contains sodium azide) is added.

This mixture is also mixed thoroughly by means of a VORTEX.

At ambient temperature, 6 units of thrombin (50 ul of a solution of Thrombase 500) are added. After agitate by means of a VORTEX, the mixture is poured into a mould coated beforehand with thrombin to facilitate the subsequent removal from the mould, and incubated at 37° C. for about 30 minutes. The product is recovered, washed and dried.

As a variant, instead of pouring the mixture into a mould the incubation is carried out in a test tube and the product formed is isolated by centrifugation.

EXAMPLE 2

Preparation of a product composed of an adduct of fibrin and elastin starting from citrated human plasma and elastin from human aorta.

10 ml of citrated human plasma are dialysed against the phosphate buffer, pH 7.4, described above, with three buffer changes each of 30 minutes.

At the end of these operations, the dialysis compartment does not contain any fibrinogen, nor yet any insoluble fibrin.

About 1 g of elastin is added, washed, swollen and equilibrated with the same buffer at 37° C.

The dialysed plasma is added to the elastin suspended in the buffer, in the proportion of 10 ml of final volume per gram, with gentle manual agitation.

The reaction is immediate and is stopped by centrifugation at 3,000 rev/min. for 2 min.

The product formed is separated from the insoluble fibrin (clot), re-precipitated and washed thoroughly with phosphate buffer.

The product has a quasi-fibrillar appearance when the suspension is subjected to gentle manual agitation and forms a membrane when the reaction is allowed to proceed.

The excess of insoluble fibrin contributes, like collagen, to the ultimate strength of the biomaterial.

FIG. 1 presents photographs showing respectively:

a) the suspension of elastin alone in the phosphate buffer, b) the initial stage of fibrin clot formation, c) the adduct after manual agitation of the mixture of elastin and plasma, and d) the adduct formed when the mixture is allowed to stand.

EXAMPLE 3

Mechanical properties and scanning electron microscopial studies of a biological patch composed of an elastin base.

Materials and Methods

1) The new artificial connective tissue or path is constituted of fibrinogen and fibronectin isolated from human plasma and of human or bovine elastin, the mixture of all of the components being subjected to the action of thrombin in the presence of calcium. To this standard preparation were added collagen, aprotinin, thiourea and heparin. The last two constituents act as agents of reticulation.

2) A structural study was carried out with the scanning electron microscope for each type of patch sample prepared.

3) The properties of mechanical resistance of each sample were tested. Their breaking load and modulus of elasticity were evaluated so as to identify the most resistant patch.

Results

1) Chemical characteristics.

The combination of elastin and products derived from fibrinogen and fibronectin in the presence of thrombin gives rise to a new, stable tissue matrix under physiological conditions of pH and ionic strength.

2) Structural characteristics.

In the scanning electron microscope the patch looks like a cross-linked network whereas isolated elastin appears as fibrils completely disconnected. Collagen and aprotinin do not alter the reticulation of the patch but are deposited in the meshes of the network. In contrast, thiourea and heparin improve reticulation. Such an electron microscopial study shows that a fibrillar constituent of plasma appears to be linked to elastin. The linkage to the fibrinogen derivative appears to be very strong throughout the entire length of the elastin molecule.

3) Physical characteristics.

The mechanical resistance of the patch determined by means of an extensometer is $16.7 \pm 2.32$ g/10 $mm^2$. The use of human elastin increases it by 63.6% ($p > 0.05$) and the addition of thiourea causes it to increase by 140% ($p < 0.001$). The patch has a modulus of elasticity of $9.28 \pm 0.69$. It is increased by 272% by the presence of human elastin and thiourea.

EXAMPLE 4

Results relating to the conditions of formation of a product according to the invention.

Figure 1A:
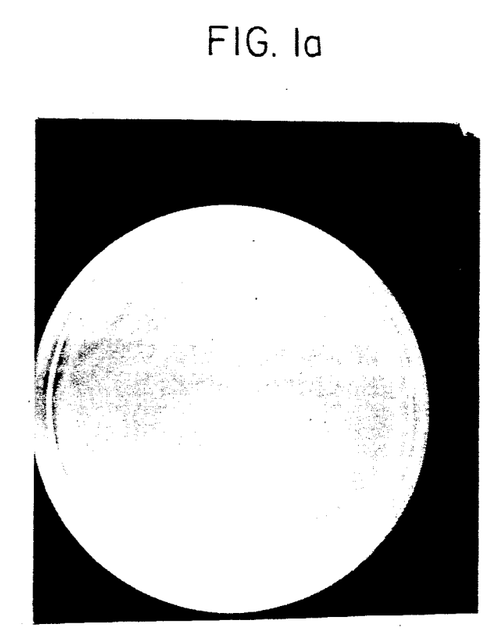
Figure 1B:
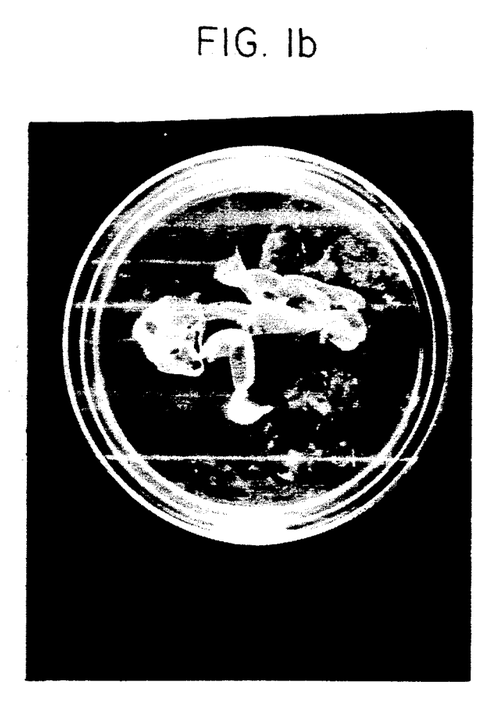
Figure 1C:
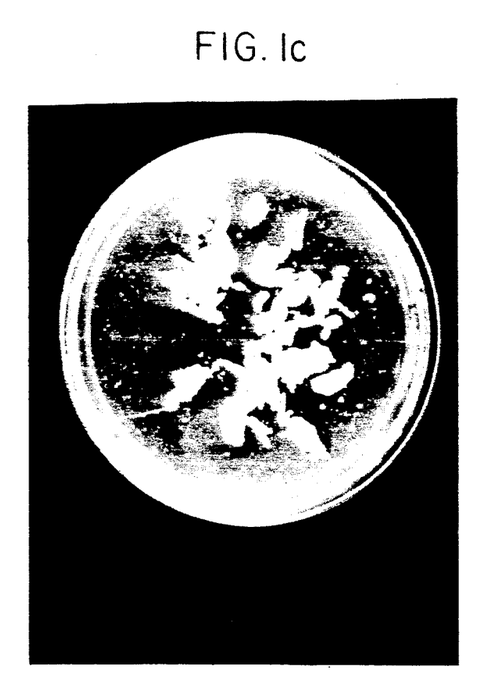
Figure 1D:
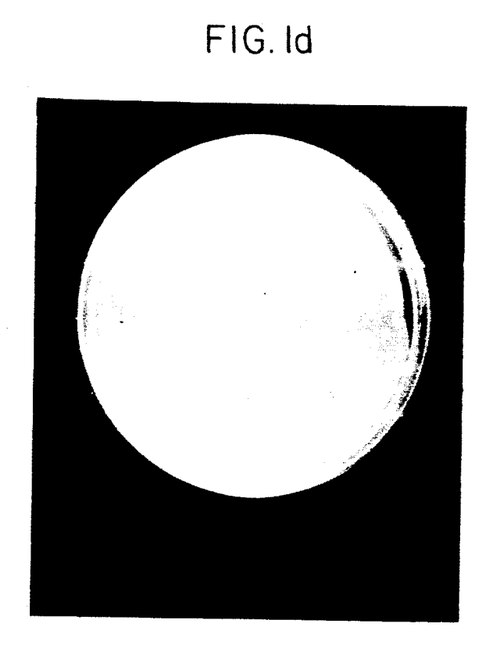
Figure 2:
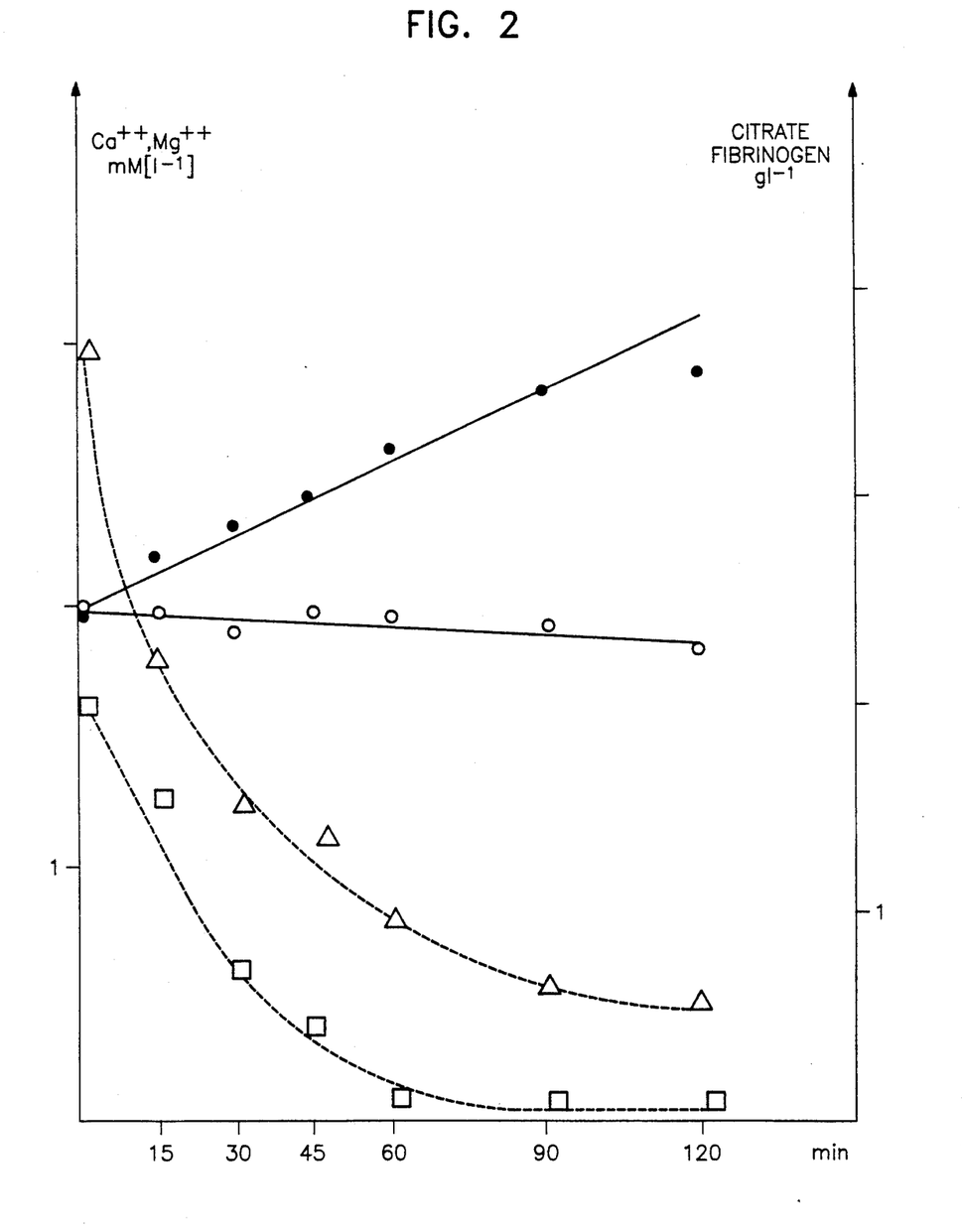

1) Study of the effect of $Ca^{++}$ ion content.

a) The results obtained are presented in FIG. 2 concerning the content of $Ca^{++}$, citrate and fibrinogen as a function of time during the dialysis of citrated plasma against a phosphate buffer.

The four curves shown in the Figure correspond to the following measurements:

curve ○ . . . ○: $Ca^{++}$ ion content when using the buffer 1 mM phosphate, 1 mM $CaCl_2$, 1 mM $MgCl_2$, 150 mM NaCl, pH 7.4, for dialysis.

curve ● . . . ●: $Ca^{++}$ ion content with the above dialysis buffer, except with 2 mM $CaCl_2$.

curve △ . . . △: Citrate content in $gl^{-1}$.

curve □ ... □: Fibrinogen content in gl$^{-1}$.

It can be seen that the Ca$^{++}$ ion content in the dialysis compartment remains unchanged when a dialysis buffer containing 1 mM of Ca$^{++}$ ion is used, even though the Ca$^{++}$ ion content of normal human plasma is about 2 mM.

Furthermore, it appears that when the same plasma is dialysed against a phosphate buffer containing 2 mM of Ca$^{++}$ ion (i.e. the Ca$^{++}$ ion concentration is the same in the interior and at the exterior of the dialysis compartment), the Ca$^{++}$ ion concentration of the plasma increases to about 3 mM after 2 hours of dialysis.

Figure 3:
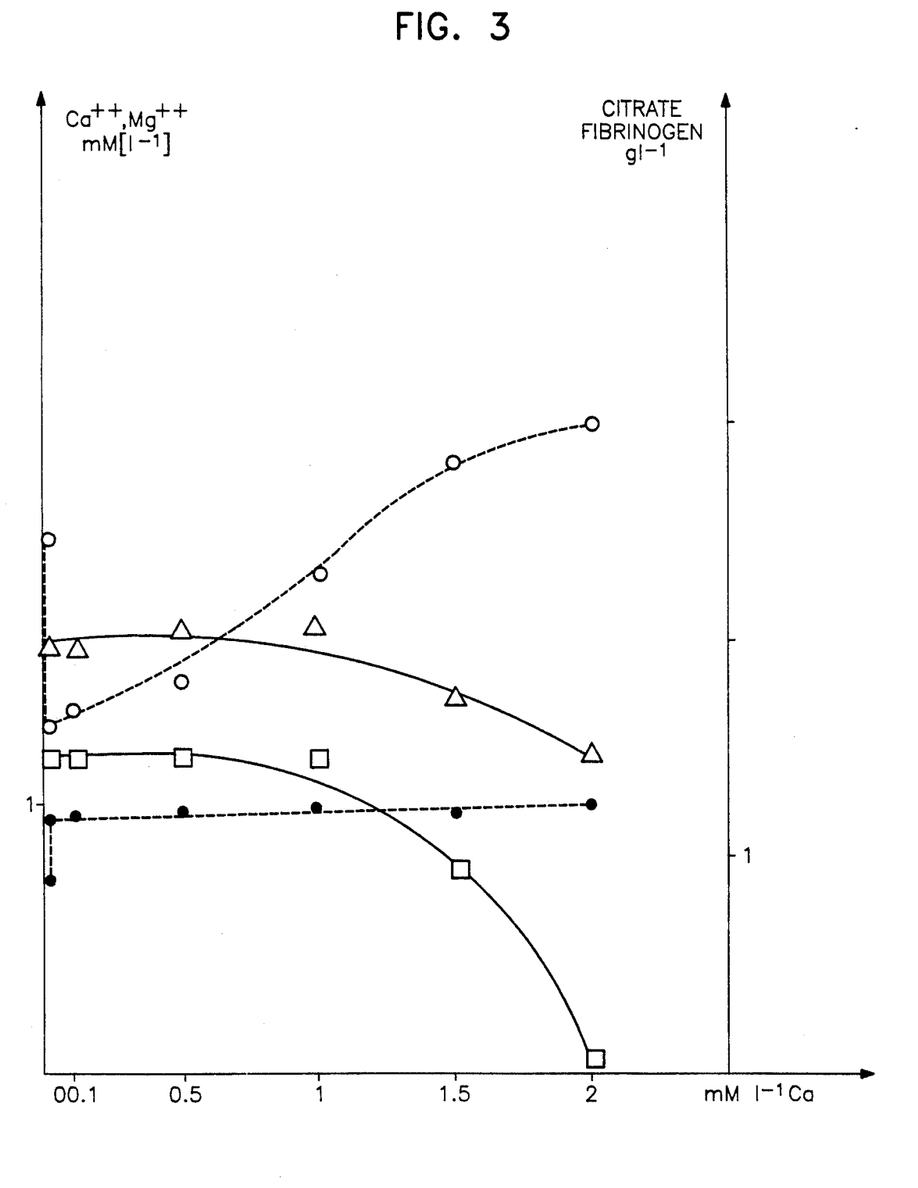

During this process, citrate is removed from the dialysis compartment and the fibrinogen is transformed into soluble fibrin, then into insoluble fibrin, according to the scheme presented above.

b) FIG. 3 presents the curves of variation of the citrate and fibrinogen concentrations as a function of the Ca$^{++}$ concentration of the dialysis buffer after 30 minutes of dialysis against a buffer of the composition: 1 mM PO$_4$; 150 mM NaCl; 1 mM MgCl$_2$; 0, 0.1, 0.5, 1.0, 1.5 and 2 mM CaCl$_2$, pH 7.4.

The different measurements are represented by the following curves:

Variation of the concentration of:
Ca$^{++}$ion: curve ○ ... ○
Mg$^{++}$ ion curve (mM): ● ... ●
citrate (gl$^{-1}$): curve △ ... △
fibrinogen (gl$^{-1}$): curve □ ... □

It can be seen that, although Mg$^{++}$ ion is unaffected, the variation of the concentration of citrate and fibrinogen depends on the Ca$^{++}$ion concentration of the dialysis buffer. The Ca$^{++}$ion content decreases slightly when the Ca$^{++}$ion concentration in the bath is zero, then it increases as the Ca$^{++}$ion content of the bath increases.

2) Study of the transformation of fibrinogen.

Figure 4:
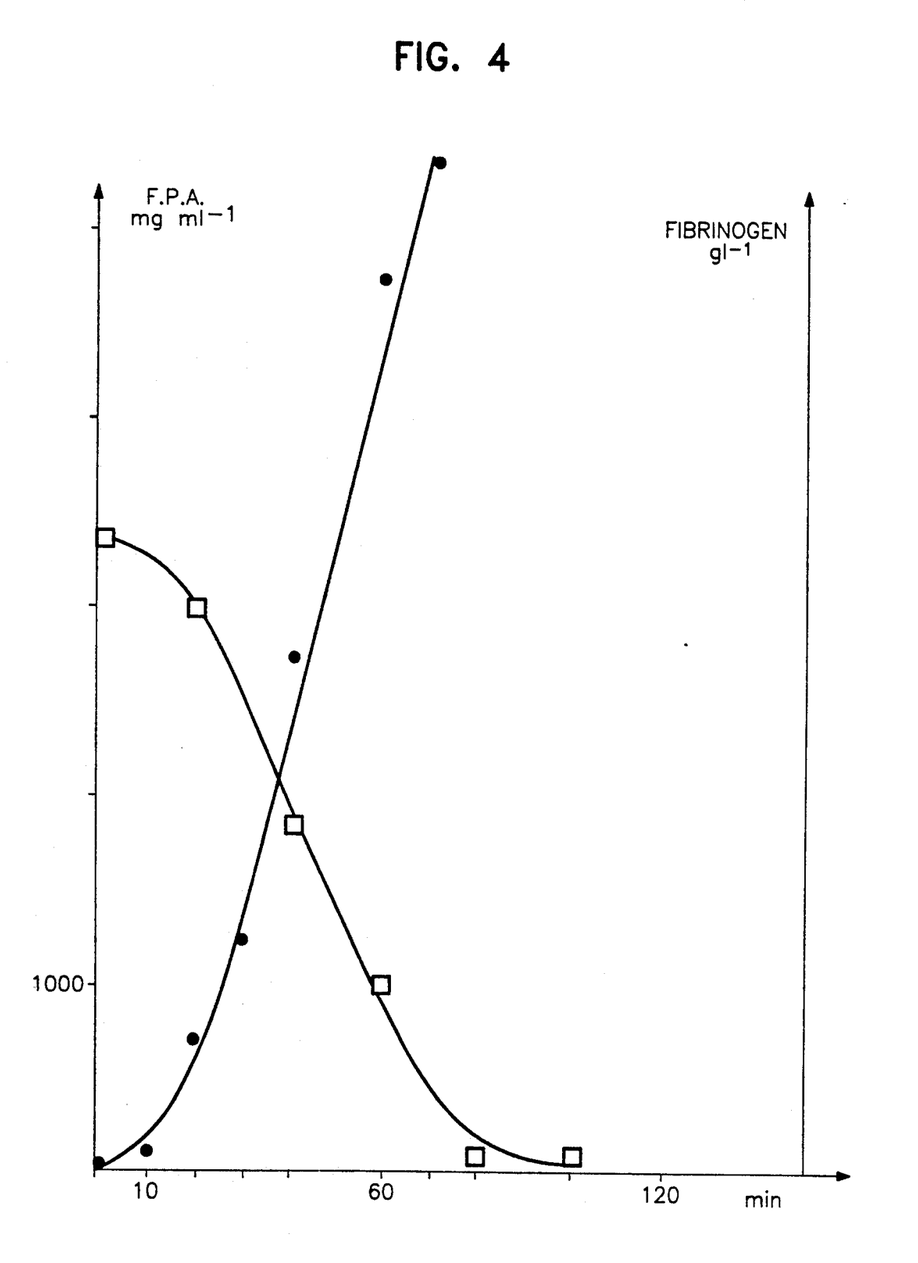

FIG. 4 presents the results obtained concerning the fibrinogen content in the dialysis compartment as a function of time (curve □ ... □) and the content of fibrinopeptides A (curve ● ... ●). It is clear that the fibrinogen content decreases whereas that of the fibrinopeptides A increases.

3) Study of the mechanism of formation of the adduct.

1, 2 or 3 ml of dialysed plasma are added to 100 mg of elastin and 12 mg of fibrinogen containing an aliquot of $^{125}$I-fibrinogen in 10 ml (total volume) of phosphate buffer, pH 7.4.

The quantities of adduct are determined after lyophilisation.

The results obtained are presented in the following Table:

|  | Plasma ml | | |
| --- | --- | --- | --- |
|  | 1 | 2 | 3 |
| Supernatant CPM 10$^{-3}$ | 300 | 300 | 300 |
| Adduct CPM 10$^{-3}$ | 750 | 800 | 910 |
| Adduct mg | 94 | 100 | 104 |

These results show that the largest proportion of the radioactivity is retained in the product formed and that a small quantity of fibrin is necessary for the formation of the adduct.

4) Effect of thrombin.

Figure 5:
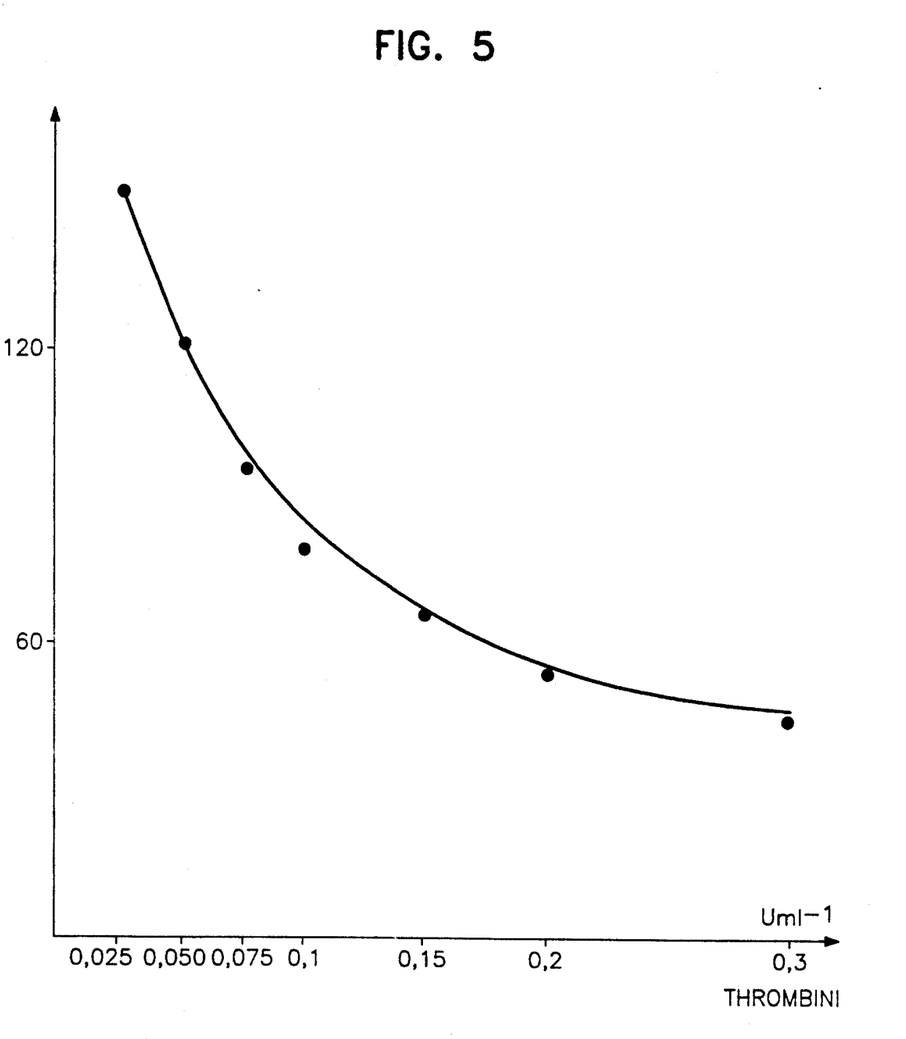

FIG. 5 shows the results obtained by studying the effect of the addition of increasing quantities of thrombin (u/ml, total volume) to a suspension of 100 mg of elastin and 15 mg of human fibrinogen labelled with $^{125}$I in 10 ml of phosphate buffer, pH 7.4. It can be seen that the formation of the adduct decreases exponentially with time.

When a given quantity of thrombin (0.1 u/ml) is added to elastin (100 mg) together with increasing quantities of $^{125}$I-fibrinogen, it is observed that the time of formation of the adduct depends on the concentration of fibrinogen.

Furthermore, when hirudin, which is a specific inhibitor of thrombin, is added to the elastin- plasma system beforehand, no effect is observed.

EXAMPLE 5

Preparation of a biological patch.

500 mg of elastin from human aorta were used and prepared as described above, and washed with an excess of phosphate buffer, pH 7.4.

The preparation is centrifuged and the elastin is recovered.

Successive addition of 2 ml of phosphate buffer, pH 7.4, 0.3 ml of aprotinin such as that sold under the name of Zymofrène by Specia, 0.2 ml of a solution containing 20 mg of thiourea per ml of phosphate buffer, pH 7.4. A dispersed suspension is formed by means of a VORTEX mixer and then are added, in the following order, 3 ml of a cryoprecipitate composed essentially of fibrinogen (40 g/l) and fibronectin (8 to 10 g/l) in phosphate buffer, 2 ml of a solution of water-soluble collagen (type I), at a concentration of 2 mg/ml, 200 microliters of a solution of thrombin (i.e. 25 units of the commercial product sold as Thrombase 500).

Between each addition the mixture was stirred vigorously with a VORTEX mixer in order to obtain a very dispersed suspension.

In an advantageous manner, the same quantity of thrombin, i.e. 25 units, is added to the mould into which the preparation is to be poured, as this facilitates removal of the biological patch formed from the mould later.

The entire mixture is incubated at 37° C. for about 30 to 60 minutes.

The biological patch is then removed from the mould and dried for about 1 hour between filter paper in order to remove the excess water from the preparation. When the patch is intended for use as a support for cell culture, the drying step is omitted.

For storage purposes, the patch is sealed in a protective envelope under nitrogen and subjected to γ-irradiation for about 6 hours (radiation of 2.5M Rads). When the product is intended for purposes of tissue repair, the sealing and irradiation steps are carried out in the presence of alcohol, the latter then being removed just before the patch is used by means of filter paper and the patch is soaked in several baths of physiological serum.

EXAMPLE 6

Application as "artificial skin": study of its suitability as an adhesive.

Experiment No. 1

Principle

A test of mechanical resistance to detachment of a square of membrane formed from a product according to example 1, pasted, on the one hand, on to the back of a sacrificed animal, and, on the other, on to a square of the animal's skin.

A hook attached to the square of skin transmits the force exerted by an increasing quantity of water derived from a burette. The complete detachment of the square of skin corresponds to the maximal force of traction expressed in g. The adhesive used consists of the cryoglobulins corresponding to the product called Transglutin which was mentioned earlier.

Procedure

A mouse weighing about 20 g is sacrificed by being confined in a receptacle containing ether.

The animal is attached to a small board with its back uppermost. A square 2 cm by 2 cm is excised and cut again into 4 squares of 1 cm by 1 cm.

A square of membrane of the invention is coated with a biological adhesive consisting of a preparation of Transglutin at a concentration of 0.05 ml per 1 cm$^2$. The square of membrane thus prepared is applied to the back of the animal which has been impregnated beforehand with thrombin (Thrombase 500).

This square is coated with Transglutin and a square of animal skin is applied on top of it.

The preparation is left undisturbed for 30 minutes, then the traction device is hooked to the centre of the square. The burette is gradually allowed to empty until the square of skin is completely detached. The quantity of water required proved to be not less than 60 g.

Results

A series of 4 measurements is carried out on the same animal and the mean of the values obtained after 30 minutes of adhesion is taken.

The values obtained lie between 62 and 116 g. None of the measurements fell below 60 g.

The results obtained illustrate the resistance of the membrane according to the invention, the membrane remaining attached to the skin up to the moment of being detached.

Study of compatibility

The components attached remain in place without difficulty and, based on observation over several weeks, no intolerance is observed.

Experiment No. 2

The adhesive properties of Transglutin were quantified by two traction devices adjusted to measure forces between 0 and 10 Newton (N).

The adhesion experiments are carried out on the skin of a mouse which has just been sacrificed.

Device No. 1

The internal dorsal cutaneous flap of the mouse is cup up into 4 squares of 1 cm$^2$ surface area. The back of the animal is impregnated with a 40 mM solution of CaCl$_2$ containing 500 U of thrombin 50 $\mu$l of Transglutin are applied to each square of skin which is then pasted immediately on to the back of the mouse. After the skin has been left to set for 40 minutes, a lifting device is attached to the square of pasted skin and sustained traction is exerted until the skin is detached. An electronic indicator measures the value of the force necessary for detachment. The average value obtained for the 70 batches of Transglutin studied was 0.98±0.15N (mean+standard deviation).

Device No. 2

The squares of mouse skin are pasted on to the base of two cylinders of 1.6 cm$^2$ surface area by means of a rapidly acting cyanoacrylic adhesive. After Transglutin has first been applied between the two flaps of skin, the bases of the cylinders are then pressed one against the other for 40 minutes. Continuous traction is then exerted. The values obtained are higher than those obtained with the first device and resulting detachment is a clear break, without an elastic component. The average value obtained for the 20 batches of Transglutin studied was 3±0.6N.

These two devices have also been used to measure the strength of adhesive bonding of a biological patch based on elastin and fibrin. A patch of 1 cm$^2$ is inserted between flaps of mouse skin and pasted to them by 50 $\mu$l of Transglutin in the presence of thrombin. In 10 experiments, the average value of the force required for detachment was 0.68±0.1N.

EXAMPLE 7

Application to Digestive Surgery

Procedure

An excision 7 to 10 mm in diameter was performed on the caecal wall of a Wistar rat or a New Zealand rabbit. The opening thus produced was closed by a patch, the diameter of which was twice as large as that of the opening and which was attached to the intestinal wall by a biological adhesive. Animals were sacrificed every 5 days upto the twentieth post-operative day, then on the thirtieth, fortieth and nintieth days. The caecum was excised and analysed both macroscopically and microscopically.

Results: At the macroscopic level, almost complete healing of the intestinal opening was observed between the fifteenth and the thirtieth post-operative day in the rabbit. A scanning electron microscopical study shows the existence of mucous hypertrophy due to the presence of villous recesses. When observed in the light microscope, this mucous membrane consists, at this stage, of a continuous epithelium of normal appearance lining a connective-vascular axis. The continuity of the muscle layer is only re-established at a later stage. The specific staining of elastin by orcein shows that this material is rejected by the serosal layer where it is surrounded with fibrous material after the thirtieth post-operative day. This material has disappeared completely in the rat by the 40th post-operative day.

Thus, the biological patch according to the invention leads to healing of injuries to the colon in the rabbit and the rat. This biomaterial inverts the usual healing phenomenology, since the restoration of the mucous layer precedes that of the muscle tissue. These promising results suggest this material as the material of choice in the treatment of digestive fistulas at every level in man.

EXAMPLE 8

Application to the culture of human vascular endothelial cells.

In the normal state, vascular endothelial cells (EC) line the internal surface of the cardiovascular system by establishing themselves on an extracellular matrix of subendothelial connective tissue (EMSCT). They form a continuous, contact-inhibited monolayer. The EC is polarized in that the vascular surface is not thrombogenic, i.e. under physiological conditions neither adhesion of platelets nor activation of the coagulation process occurs.

The EC are isolated from the vein of the umbilical cord by moderate digestion with collagenase, added at high density on the surface of a polystyrene dish, 35 mm in diameter and covered with a biological patch according to the invention, and incubated in a culture medium containing 30% human serum according to a previously described technique (Biol. Cell. 1984, 52, 9-20). The cells proliferate and attain confluence within 5 to 6 days. The confluent ECs are examined under the optical microscope after being stained and in the electron microscope, and are seen to possess the morphological characteristics of ECs. Their endothelial nature is confirmed by the intracellular presence of a specific marker, the Willebrand factor. In addition, human platelets do not adhere to their surface. In contrast, platelets adhere strongly to the thrombogenic surface of the adduct not covered with EC.

The adduct thus behaves like an EMSCT which promotes the proliferation of a monolayer of non-thrombogenic EC. The properties of the adduct suggest it as an EMSCT of choice for promoting the culture of human EC and for the development of vascular prostheses which are non-thrombogenic and biocompatible.

EXAMPLE 9

Study of thrombogenic properties at the interface between blood and a biological patch based on elastin and fibrin.

The interaction of blood with thrombogenic surfaces leads to the adhesion of platelets, the secretion of the contents of their granules and the formation of platelet aggregates. The activation of coagulation leads to the generation of thrombin and the polymerisation of fibrinogen into fibrin. These reactions, which in a blood vessel lead to a pathological thrombosis, are desirable in the case of tissue repair for the binding of a biological patch based on elastin, fibrin and, possibly, collagen when used in vascular, digestive or skin surgery.

Human blood is collected in ACD, the platelets are separated, washed, labelled with $^{111}$indium and resuspended in Tyrode physiological medium containing human albumin. The platelet suspension is placed in contact with a patch of known surface area covering a polystyrene Petri dish under stationary conditions for 30 minutes. The adhesion of the platelets to the surface of the polystyrene covered by the patch is compared to adhesion to the polystyrene after proteins have or have not been absorbed on to it.

The patch based on elastin, fibrin, fibronectin and collagen provides the most thrombogenic surface: 42,300±1,600 platelets per mm$^2$ (mean±SD, n=6). In the absence of absorbed proteins, 1600±800 platelets adhere to the polystyrene per mm$^2$. Pretreatment of the polystyrene surface with 0.35% albumin for 30 minutes reduces the adhesion of platelets to 4,800±200 per mm$^2$.

During adhesion the platelets are activated, change their form, spread out and secrete the contents of their granules, serotonin and platelet factor 4, into the extracellular medium.

The patch activates the intrinsic pathway of coagulation. The exposure of citrated human plasma to the surface of the patch causes activation and the consumption of Factor XII of the contact phase. This results in a prolongation of the time of activated cephalin which measures the overall coagulation of plasma.

In conclusion, the interaction of the constituents of blood, platelets and proteins involved in coagulation, at the surface of a patch of artificial connective tissue composed of elastin, collagen, fibrin and fibronectin leads to the activation of platelets and coagulation. The thrombogenic properties of the patch suggest its use as a means to repair tissue injuries.

We claim:

1. An elastin containing composition comprising fibronectin and wherein elastin is covalently bound to fibrin monomers.

2. An elastin containing composition consisting essentially of a synthetic compound resulting from the reaction of fibrin monomers with elastin.

3. An elastin containing composition obtained by reacting elastin with cryoglobulins, in the presence of thrombin and Ca$^{++}$.

4. An elastin containing composition according to claim 3 wherein said cryoglobulins are selected from the group consisting of
   cryoglobulins corresponding to the lyophilized fraction called antihemophilic A, the latter containing about 10 to 15 g/l of fibrinogen and about 2 to 4 g/l of fibronectin,
   cryoglobulins obtained during the isolation of concentrated Factor VIII, the latter which contains about 9 to 20 g/l of fibrinogen and about 10 to 14 g/l of fibronectin, and
   cryoglobulins composed of a lyophilized protein complex called transglutin, which contains about 50 to 90 g/l of fibrinogen and about 8 to 15 g/l of fibronectin.

5. An elastin containing composition obtained by reacting plasma with elastin, in the presence of thrombin and Ca$^{++}$.

6. An elastin containing composition according to claim 1, further comprising at least one additive selected from the group consisting of collagen, thiourea, cellulose derivatives, calcium alginate, sodium ethylmercrylthiosalicylate, FVIII complex (antihemophilic A), the latter containing about 10 to 15 g/l of fibrinogen and about 2 to 4 g/l of fibronectin, von Willebrand factor, thrombospondin and laminin.

7. An elastin containing composition according to claim 2, wherein the elastin and fibrin monomers are of human origin.

8. An elastin containing composition according to claim 2, wherein the elastin and fibrin monomers are of animal origin.

9. An elastin containing composition consisting essentially of a synthetic compound resulting from the reaction of fibrinogen with elastin, in the presence of thrombin and Ca$^{++}$.

10. An elastin containing composition according to claim 6, wherein said elastin containing composition is an adduct in the form of a cross-linked network.

11. A process of preparing an elastin containing composition comprising the steps of:
   contacting with fibrinogen a suspension of elastin in a buffer containing Ca$^{++}$;

adding thrombin to the resultant mixture to form a reaction mixture;

incubating the reaction mixture; and then separating the resulting elastin-fibrin monomers adduct.

12. A process according to claim 11, wherein said fibrinogen is provided by plasma.

13. A process according to claim 11, wherein said fibrinogen is provided by cryoglobulins.

14. A process according to claim 11, comprising the step of pouring said reaction mixture into a mold prior to incubation, and comprising the step of recovering, washing and drying the resulting adduct to enable the use thereof as a biomaterial.

15. A process according to claim 11 further comprising the step of adding, prior to incubation, at least one additive selected from the group consisting of collagen, thiourea, cellulose derivatives, calcium alginate, sodium ethylmercrylthiosalicylate, FVIII complex (antihemophilic A), the latter containing about 10 to 15 g/l of fibrinogen and about 2 to 4 g/l of fibronectin, von Willebrand factor, thrombospondin and laminin.

16. The process according to claim 11, wherein said incubation step is carried out at about 37° C. in a buffer of a pH of about 7.4, the $Ca^{++}$ content of which is on the order of 2 mM.

17. An artificial connective tissue comprising the elastin containing composition according to claim 3.

18. An artificial connective tissue comprising the elastin containing composition according to claim 5.

19. An artificial connective tissue comprising the elastin containing composition according to claim 2.

20. An artificial connective tissue comprising the elastin containing composition according to claim 9.

21. A method of preparing an artificial connective tissue which comprises the use of an elastin containing composition consisting essentially of a synthetic compound resulting from the reaction of fibrin monomers with elastin.

22. A method of preparing an artificial connective tissue which comprises the use of an elastin containing composition, wherein elastin is covalently bound to fibrin monomers.

23. A physical support for cell cultures comprising the elastin containing composition according to claim 2.

24. A physical support for cell cultures comprising the elastin containing composition according to claim 9.

25. A physical support for cell cultures comprising the elastin containing composition according to claim 3.

26. A physical support for cell cultures comprising the elastin containing composition according to claim 5.

27. Means for incorporating enzymes or enzyme inhibitors comprising the elastin containing composition according to claim 2.

28. Means for incorporating enzymes or enzyme inhibiting comprising the elastin containing composition according to claim 9.

29. Means for incorporating enzymes or enzyme inhibitors comprising the elastin containing composition according to claim 3.

30. Means for incorporating enzymes or enzyme inhibitors comprising the elastin containing composition according to claim 5.

31. A kit for cell culture comprising a receptacle containing the elastin containing composition according to claim 2.

32. A kit for tissue repair comprising a storage envelope containing the elastin containing composition according to claim 2 and a container containing a biological adhesive.

* * * * *